(12) United States Patent
Ziv-Av

(10) Patent No.: US 6,458,089 B1
(45) Date of Patent: Oct. 1, 2002

(54) METHODS AND DEVICES FOR REDUCING TREMBLING

(76) Inventor: Amir Ziv-Av, 3 Hanasi, Kiryat Ono (IL)

( * ) Notice: Subject to any disclaimer, the term of this patent is extended or adjusted under 35 U.S.C. 154(b) by 0 days.

(21) Appl. No.: 09/553,901

(22) Filed: Apr. 20, 2000

(51) Int. Cl.[7] .......................... A61B 5/103; A61B 5/117
(52) U.S. Cl. ...................................................... 600/595
(58) Field of Search ................................ 600/595, 552; 601/80, 104; 128/878, 897, 898; 623/24

(56) References Cited

U.S. PATENT DOCUMENTS

| | | | | |
|---|---|---|---|---|
| 4,237,873 A | * | 12/1980 | Terry et al. ..................... 602/20 |
| 4,306,291 A | * | 12/1981 | Zilm et al. ................... 600/552 |
| 4,842,607 A | | 6/1989 | Repperger et al. |
| 5,058,571 A | | 10/1991 | Hall |
| 5,201,772 A | * | 4/1993 | Maxwell ....................... 623/24 |
| 5,231,998 A | * | 8/1993 | Rosen et al. ................. 128/878 |
| 5,265,619 A | * | 11/1993 | Comby et al. ............... 600/595 |
| 5,293,879 A | * | 3/1994 | Vonk et al. .................. 600/595 |
| 5,772,611 A | * | 6/1998 | Hocherman .................. 600/595 |
| 6,106,491 A | * | 8/2000 | Gianutsos .................... 601/104 |
| 6,213,961 B1 | * | 4/2001 | Reinsma ....................... 601/80 |

* cited by examiner

*Primary Examiner*—Kevin Shaver
*Assistant Examiner*—Brian Szmal
(74) *Attorney, Agent, or Firm*—Mark M. Friedman

(57) ABSTRACT

The present invention is a method and device for reducing trembling of a limb of a human subject. The method comprises suspending a mass from the limb via a suspension configuration. The suspension configuration having an effective spring constant and/or a non-zero coefficient of damping in at least one direction such that the mass is driven to oscillate in the at least one direction out of phase relative to the trembling motion. A further embodiment includes a motion sensor to sense the motion of the limb, an actuator to generate the damping force, and a control unit that is responsive to the motion sensor and actuator to generate a damping force that alleviates trembling.

14 Claims, 4 Drawing Sheets

METHODS AND DEVICES FOR REDUCING TREMBLING

FIELD AND BACKGROUND OF THE INVENTION

The present invention relates to health care accessories and, in particular, it concerns methods and devices for reducing trembling of the limbs such as is commonly experienced by sufferers of Parkinson's disease or the like.

A significant proportion of the population suffer from trembling or shaking, referred to technically as "tremor". Tremor is a common medical symptom consisting of a rhythmic oscillation of a part of the body around a fixed point. Tremors most often involve the distal parts of limbs, although they can also affect the head, tongue, jaw, or rarely the trunk. The mechanisms by which tremors are generated have been poorly understood. It is long been thought, however, that tremors are brought about by interactions of nerve cells in complex, incompletely understood circuits within the brain.

Tremors are subdivided clinically in a number of ways according to distribution, frequency, amplitude, and/or relationship to volitional movement. One type of tremor that is commonly recognized is known as tremor at rest. This is a coarse tremor with an average rate of 4 to 5 beats per second and is a frequent feature of Parkinson's disease. This type of tremor gains its name from its relationship to volitional movement. This tremor typically occurs when a limb is at rest; willed movement temporarily suppresses the tremor. In some cases, the tremor is constant; in others it varies from time to time and may extend from one group of muscles to another as the disease progresses.

Another type of tremor, termed action tremor or intention tremor, is associated with cerebellar disorders. For example, patients with multiple sclerosis, which frequently involves the cerebellum and its connections, sometimes develop a coarse tremor which is brought on by activity and absent at rest. Other cerebellar disorders, such as the inherited cerebellar degenerations, also may have action tremor as a major symptom.

Another, tremor brought out by activity is known as essential (or essential-familial) tremor. This tremor sometimes begins in childhood but usually occurs later and persists through adult life, often affecting several members of a family (hence its name). It is known that essential-familial tremors can be suppressed by primidone or CNS-active β-adrenergic blocking agents, such as propranolol.

A number of other types of tremors also exist, including physiologic tremor (typically associated with excitement and other hyperandrenergic states; stage fright is a typical example). Numerous reviews of the various tremor states exist, such as can be found in Chapter 15 (entitled "Paralysis and Other Disorders of Movement") of Harrison's Principles of Internal Medicine 11th Edition, Brownwald et al., Eds., McGraw-Hill Book Company, New York, 1987.

Unfortunately, many patients with tremor are resistant to current therapies. The tremor of patients with Parkinson's disease may be only partially responsive to the actions of trihexyphenidyl and related anticholinergic drugs or to dopamine agonists. Additionally, unacceptable central nervous system side effects, including confusion and hallucinations, are sometimes associated with current Parkinson's disease treatments. Treatments of the tremor of cerebellar disease are also generally ineffective.

In the absence of safe and effective treatments to cure or suppress the aforementioned trembling symptoms of all types, is would be highly advantageous to provide a device and corresponding method for reducing the amplitude of the trembling motion of a limb of a human subject.

SUMMARY OF THE INVENTION

The present invention is a method and device for reducing trembling of a limb of a human subject.

According to the teachings of the present invention there is provided, a method for reducing an amplitude of a trembling motion of a part of a human limb in at least one direction and at at least one frequency, the method comprising suspending a mass from the limb via a suspension configuration, the suspension configuration having an effective spring constant and/or a non-zero coefficient of damping in the at least one direction such that the mass is driven to oscillate in the at least one direction out of phase relative to the trembling motion, thereby reducing the amplitude of the trembling motion.

There is also provided according to the teachings of the present invention, a device for reducing an amplitude of a trembling motion of a part of a human limb in at least one direction and at at least one frequency, the device comprising: (a) a mass; and (b) a suspension configuration configured for suspending ;the mass relative to the part of the limb, the suspension configuration being configured to provide a given effective spring constant and/or a non-zero coefficient of damping between the limb and the mass in the at least one direction such that, when attached to the part of the limb, the mass is driven to oscillate in the at least one direction out of phase relative to the trembling motion, thereby reducing the amplitude of the trembling motion.

There is also provided according to the teachings of the present invention, a method for reducing an amplitude of a trembling motion of a part of a human limb in at least one direction, the method comprising: (a) sensing motion of the limb in the at least one direction; and (b) generating a variable force in the at least one direction, the variable force being varied in such a manner as to reduce an amplitude of the trembling motion.

Finally, there is also provided according to the teachings of the present invention, a device for reducing an amplitude of a trembling motion of a part of a human limb in at least one direction, the device comprising: (a) a bracket for mounting substantially rigidly on the limb; (b) a motion sensor associated with he bracket and configured to produce an output indicative of motion of the limb in the at least one direction; (c) an actuator associated with the bracket and configured to selectively generate a force in the at least one direction; and (d) a control unit associated with both the motion sensor and the actuator, the control unit being responsive to the output to actuate the actuator in a manner such as to reduce an amplitude of the trembling motion.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and device for reducing trembling of a limb of a human subject.

The principles and operation of devices and methods according to the present invention may be better understood with reference to the drawings and the accompanying description.

Figure 1:
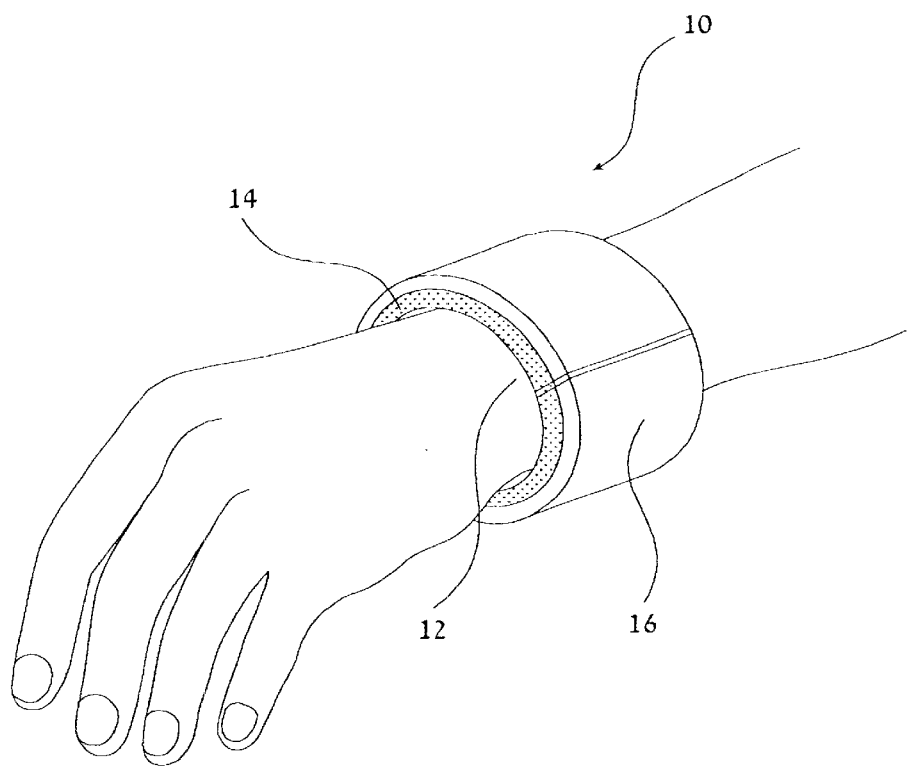
FIG. 1 is an isometric view of a first embodiment of a device, constructed and operative according to the teachings of the present invention, for reducing the amplitude of trembling of a limb of a human subject.
Figure 2:
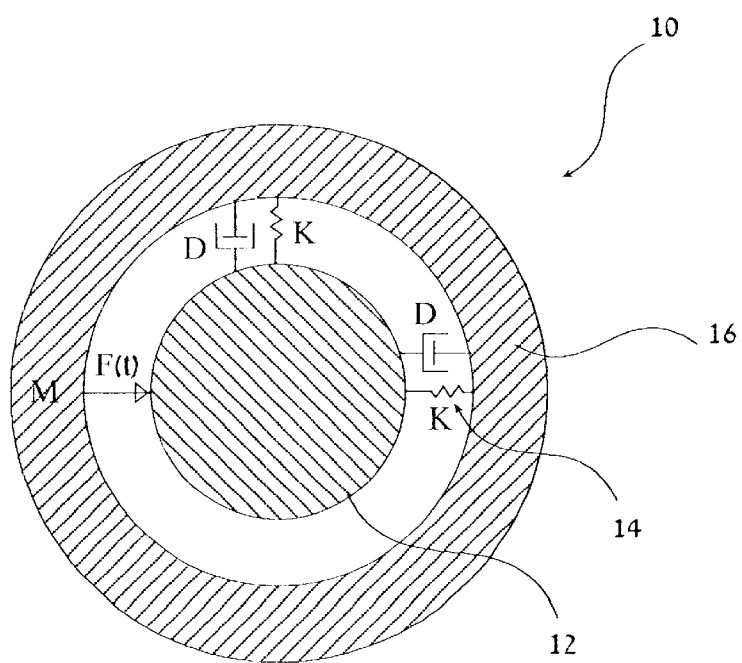
FIG. 2 is a schematic cross-sectional view taken through the device of FIG. 1.

Referring now to the drawings, FIGS. 1 and 2 show a device, generally designated 10, for reducing. an amplitude of a trembling motion of a part of a human limb 12 in at least one direction (referred to for convenience as the x-direction) and at at least one frequency (referred to for convenience as λ).

Generally speaking, device 10 includes a suspension configuration 14 configured for suspending a mass 16 relative to the part of the limb 12. Suspension configuration 14 is configured to provide a given effective spring constant K and/or a given non-zero coefficient of damping D, between limb 12 and mass 16 in at least the x-direction such that, when attached to the part of limb 12, the trembling motion causes mass 16 to oscillate in the x-direction out of phase relative to the trembling motion, thereby reducing the amplitude of the trembling motion.

Figure 4:
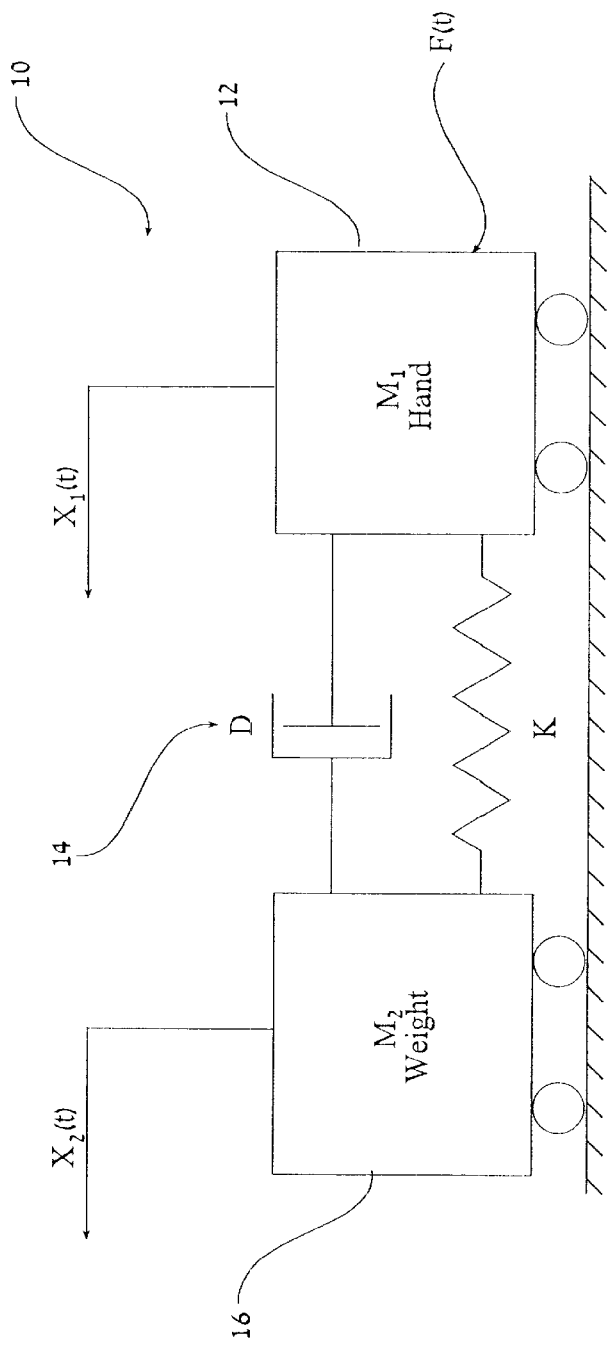
FIG. 4 is a schematic representation of the parameters used in one-dimensional equations of motion for the device of FIG. 1.

Before addressing details of specific implementations of the present invention, the theoretical basis of this embodiment of the invention will be discussed briefly with reference to FIG. 4.

Thus, the effective mass of the part of the limb 12 is taken to be $M_1$ and hat of weight 16 is taken to be $M_2$. The positions in the x-direction of these two weights relative to a given starting position as a function of time are termed $x_1(t)$ and $x_2(t)$, respectively. The spring value between the two weights is taken to be K while the damping coefficient is taken to be D.

Using this terminology, if the trembling motion is actuated by a force F(t), the equation of motion for the part of limb 12 may be written:

$$F(t) - M_1 \frac{\partial^2 x_1}{\partial t^2} - D \frac{\partial (x_1 - x_2)}{\partial t} - K(x_1 - x_2) = 0$$

Similarly, the equation of motion for weight 16 may be written:

$$0 - M_2 \frac{\partial^2 x_2}{\partial t^2} - D \frac{\partial (x_2 - x_1)}{\partial t} - K(x_2 - x_1) = 0$$

In a first approximation, the actuating force F(i) may be assumed to be a sinusoidal function of given frequency λ. This frequency, as well as approximations to the weight of the limb and the magnitude of the force, can readily be measured for a given patient. The above equations can then be solved to find values of K and/or D which will reduce xi and its derivatives, thereby reducing the amplitude of the oscillation of the trembling motion.

In many cases, it may be sufficient to provide a suspension configuration 14 with one or other of spring and damping properties, i.e., with either D=0 or K=0. In other cases, it may be preferred to construct suspension configuration 14 so as to provide non-zero values of both the spring and damping coefficients. The devices of the present invention are preferably configured to reduce the amplitude of the trembling motion by a number of tens of percent.

The theory underlying this embodiment of the present invention has been presented here as a one-dimensional model. In many cases, the trembling motion is largely limited to a single direction such that the one-dimensional model is adequate. However, an equivalent but independent set of equations can clearly be obtained and solved for motion in a perpendicular "y-direction".

In structural terms, the desired spring properties are typically provided by selection of suitable resilient polymer material. Alternatively, or additionally, the effective spring properties may be varied for a given material by structural modification of the suspension configuration 14. The desired damping properties are typically provided by inclusion of a viscous medium or polymers with suitable properties. The details of a suitable structure to provide a given set of spring and damping properties may readily be derived by minimal experimentation by one ordinarily skilled in the art.

In certain cases, the weight and suspension system may be implemented together as a single material with variable density such that a less dense inner portion provides the required suspension configuration properties while the more dense outer portion provides the required weight.

Figure 3A:
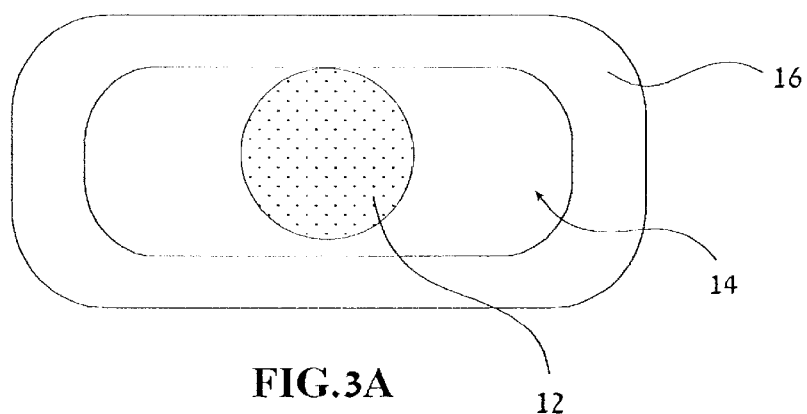
FIGS. 3A–3C are cross-sectional views similar to FIG. 2 showing three variant implementations of the device of FIG. 1.
Figure 3B:
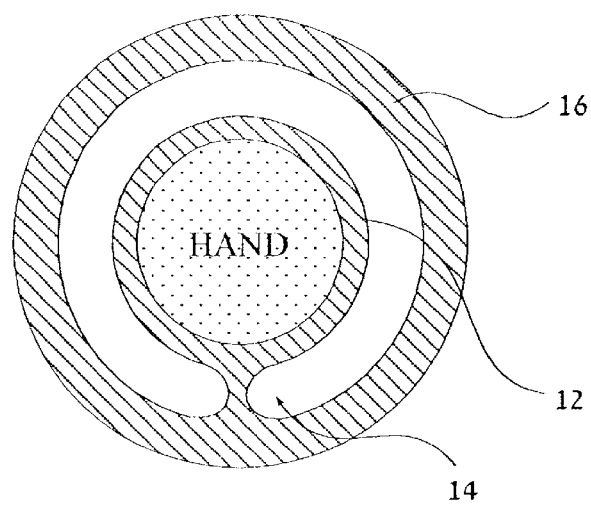
Figure 3C:
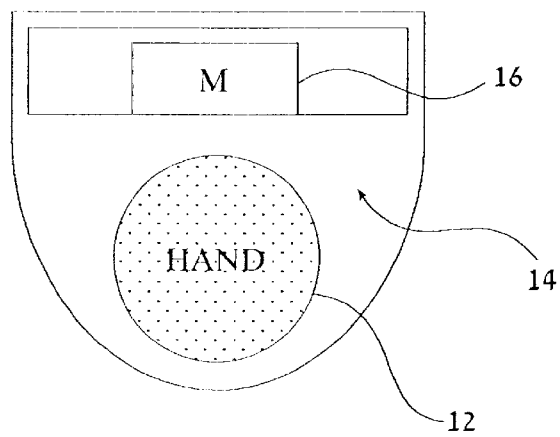

Turning now briefly to FIGS. 3A–3C, a number of variants of the embodiment of FIG. 1 will be discussed. Firstly, with reference to FIG. 3A, it should be noted that the neither suspension configuration 14 nor the distribution of weight 16 need be symmetrical, or even continuous, about limb 12. By way of example, in the variant of FIG. 3A, suspension configuration 4 is configured to provide spring properties substantially exclusively in a single direction (horizontally as shown) while the thickness of suspension configuration 14 is reduced to a minimum in the perpendicular direction.

As mentioned earlier, the required spring properties of suspension configuration 14 may be provided by structural modification. For example, the weight 16 may be connected to an inner mounting structure via a number of relatively thin connecting portions. Such an example is illustrated in FIG. 3B. In this case of a single connecting portion, the motion of the weight relative to the limb of the subject is a pivotal oscillation, the connecting portion acting as a spring-hinge.

It should also be noted that the present invention is not limited to implementations in which the "spring constant" and the "damping coefficient" are constants. Thus, the suspension configuration may be configured to provide various more complex spring and/or damping properties.

By way of an extreme example, represented schematically in FIG. 3C, friction may be used to provide a force resisting the trembling motion. In this case, the force is constant, being a function only of the weight and the friction coefficient between the suspension configuration and the weight. The force is exerted when the acceleration of the limb exceeds a threshold value.

Figure 5:
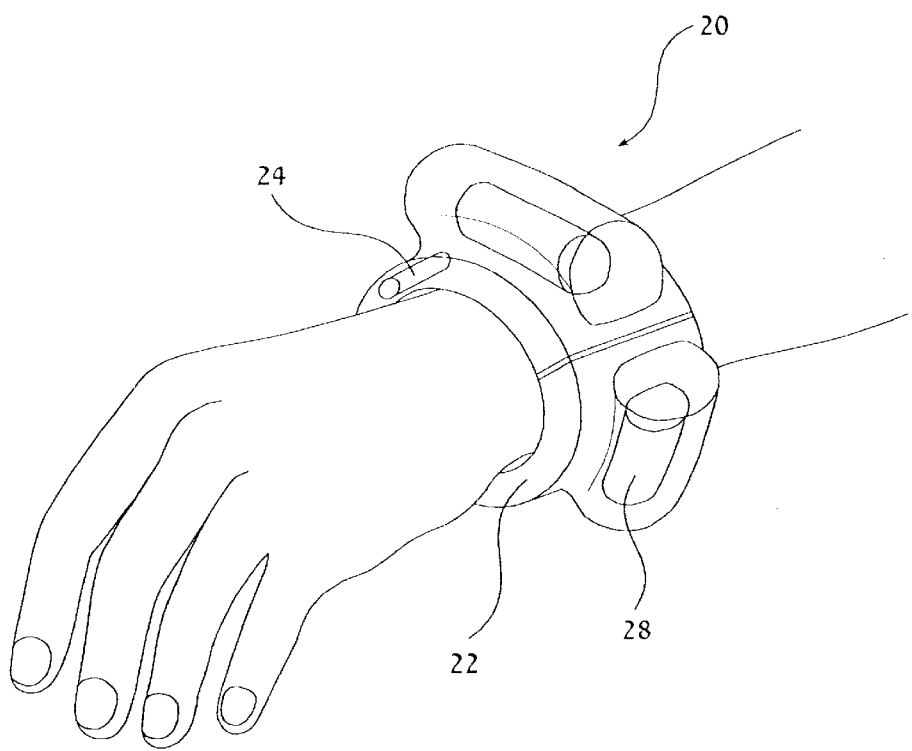
FIG. 5 is an isometric view of a second embodiment of a device, constructed and operative according to the teachings of the present invention, for reducing the amplitude of trembling of a limb of a human subject.
Figure 6:
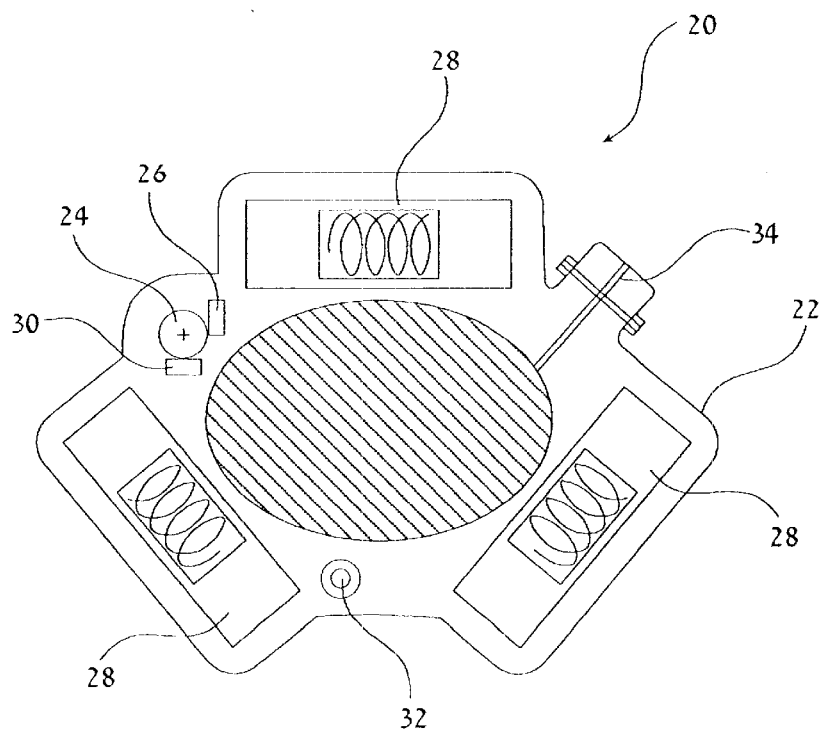
FIG. 6 is a schematic cross-sectional view taken through the device of FIG. 5.

Turning now to FIGS. 5 and 6, a second embodiment of a device, generally designated 20, for reducing an amplitude of a trembling motion of a art of a human limb 12 is shown. This embodiment differs from the first embodiment primarily in that it replaces the passive mechanical elements with an active system for producing forces to partially or entirely cancel the trembling motion.

In structural terms, device 20 includes a bracket 22 configured for mounting substantially rigidly on limb 12. Bracket 22, preferably implemented as a housing 22, includes a motion sensor 24 configured to produce an output indicative of motion of the limb in at least one direction, termed the x-direction, and at least one actuator 26 configured to selectively generate a force in at least the x-direction. A control unit 28 is responsive to the output of sensor 24 to actuate the at least one actuator 26 in a manner such as to reduce an amplitude of the trembling motion.

It will be readily appreciated by one ordinarily skilled in the art that the aforementioned components may be selected from a wide range of readily available components well known for use in other applications. For example, motion sensor 24 may be selected from a wide range of commercially available motion sensors such as various types of accelerometer and the like. Optionally, control unit 28 may be configured to perform preprocessing on the sensor output to filter out non-tremor-associated motion such as by filtering techniques discussed in the above-referenced U.S. Pat. Nos. 4,306,291 and 5,265,619.

Actuators 28 may be any component capable of selectively generating a force, typically in an oscillatory manner. Typical examples include, but are not limited to, linear motors and rotary motors with an eccentric weight. For one-dimensional implementations, a single actuator 28 may be sufficient. However, in order to avoid application of a turning moment to the limb, it may be preferable to employ two parallel actuators on opposite sides of the limb. For two-dimensional compensation, at least two non-parallel actuators are provided. The triangular deployment of three actuators 28 as illustrated here is believed to be advantageous for its ability to provide low turning-moment forces in any direction, although a rectangular arrangement of four actuators may provide further advantages of simplicity of calculation and implementation.

Power for the various electrical components is typically provided by a battery 30, also located within housing 22. Attachment of the device to the limb may conveniently be achieved by providing housing 22 with a hinge 32 and a catch 34 for holding the housing closed as shown.

Finally, it should be noted that the features of the above described embodiments are not exclusive. Thus, for example, the motion sensor and control unit of the second embodiment could be used to advantage with an adjustment mechanism of an otherwise passive device of the type described with reference to the first embodiment, thereby providing automatic adaptation to the required dynamic characteristics for a given individual.

It will be appreciated that the above descriptions are intended only to serve as examples, and that many other embodiments are possible within the spirit and the scope of the present invention.

What is claimed is:

1. A method for reducing an amplitude of a trembling motion of a part of a human limb in at least one direction and at at least one frequency, the method comprising suspending a mass from the limb via a suspension configuration, said suspension configuration having an effective spring constant in the at least one direction such that the mass is driven to oscillate in the at least one direction out of phase relative to the trembling motion, thereby reducing the amplitude of the trembling motion.

2. The method of claim 1, wherein said suspension configuration additionally has a non-zero coefficient of damping in the at least one direction.

3. A device for reducing an amplitude of a trembling motion of a part of a human limb in at least one direction and at at least one frequency, the device comprising:

(a) a mass; and (b) a suspension configuration configured for suspending said mass relative to the part of the limb, said suspension configuration being configured to provide a given effective spring constant between the limb and said mass in the at least one direction such that, when attached to the part of the limb, said mass is driven to oscillate in the at least one , direction out of phase relative to the trembling, motion, thereby reducing the amplitude of the trembling motion.

4. The device of claim 3, wherein said suspension configuration is additionally configured to provide a non-zero coefficient of damping between the limb and said mass in the at least one direction.

5. A method for reducing an amplitude of a trembling motion of a part of a human limb in at least one direction and at at least one frequency, the method comprising suspending a mass from the limb via a suspension configuration, said suspension configuration having a non-zero coefficient of damping in the at least one direction such that the mass is driven to oscillate in the at least one direction out of phase relative to the trembling motion, thereby reducing the amplitude of the trembling motion.

6. The method of claim 5, wherein said suspension configuration additionally has an effective spring constant in the at least one direction.

7. A device for reducing an amplitude of a trembling motion of a part of a human limb in at least one direction and at at least one frequency, the device comprising:

(a) a mass; and (b) a suspension configuration configured for suspending said mass relative to the part of the limb, said suspension configuration being configured to provide a given non-zero coefficient of damping between the limb and said mass in the at least one direction such that, when attached to the part of the limb, said mass is driven to oscillate in the at least one direction out of phase relative to the trembling motion, thereby reducing the amplitude of the trembling motion.

8. The device of claim 7, wherein said suspension configuration is additionally configured to provide a given effective spring constant between the limb and said mass in the at least one direction.

9. A method for reducing an amplitude of a trembling motion of a part of a human limb in at least one direction, the method comprising:

(a) sensing motion of the limb in said at least one direction; and (b) employing a non-tethered device supported exclusively by attachment to the limb to generate a variable force in said at least one direction, said variable force being varied in such a manner as to reduce an amplitude of the trembling motion.

10. The method of claim 9, wherein said variable force is generated inertially by causing acceleration of a mass relative to the limb.

11. The method of claim 10, wherein acceleration of said mass is generated by a motor.

12. A non-tethered device for reducing an amplitude of a trembling motion of a part of a human limb in at least one direction, the device comprising:

(a) a bracket for mounting substantially rigidly on the limb, said bracket being supported exclusively by attachment to the limb;

(b) a motion sensor associated with said bracket and configured to produce an output indicative of motion of the limb in said at least one direction;

(c) an actuator associated with said bracket and configured to selectively generate a force in said at least one direction; and (d) a control unit associated with both said motion sensor and said actuator, said control unit being responsive to said output to actuate said actuator in a manner such as to reduce an amplitude of the trembling motion.

13. The device of claim 12, wherein said actuator includes an inertial actuator operative to generate acceleration of a mass relative to the limb.

14. The device of claim 13, wherein said actuator includes at least one motor.

* * * * *